(12) United States Patent
Boer et al.

(10) Patent No.: US 7,084,150 B2
(45) Date of Patent: Aug. 1, 2006

(54) ANALOGS AND PRODRUGS OF BUPRENORPHINE

(75) Inventors: F. Peter Boer, Boyton Beach, FL (US); Robert Kupper, East Greenwich, RI (US)

(73) Assignee: Euro-Celtique S.A., Luxembourg (LU)

( * ) Notice: Subject to any disclaimer, the term of this patent is extended or adjusted under 35 U.S.C. 154(b) by 10 days.

(21) Appl. No.: 10/692,662

(22) Filed: Oct. 24, 2003

(65) Prior Publication Data

US 2004/0192714 A1    Sep. 30, 2004

Related U.S. Application Data

(60) Provisional application No. 60/421,347, filed on Oct. 25, 2002.

(51) Int. Cl.
   *C07D 419/02*    (2006.01)
   *A61K 31/438*    (2006.01)

(52) U.S. Cl. .......................................... 514/279; 546/39

(58) Field of Classification Search .......... 546/39, 546/41; 514/279
See application file for complete search history.

(56) References Cited

U.S. PATENT DOCUMENTS

| | | | |
|---|---|---|---|
| 4,588,580 A | 5/1986 | Gale et al. | 424/21 |
| 4,806,341 A | 2/1989 | Chien et al. | 424/448 |
| 5,026,556 A | 6/1991 | Drust et al. | 424/449 |
| 5,069,909 A | 12/1991 | Sharma et al. | 424/449 |
| 5,225,199 A | 7/1993 | Hidaka et al. | 424/443 |
| 5,240,711 A | 8/1993 | Hille et al. | 424/448 |
| 5,908,846 A | 6/1999 | Bungaard et al. | 514/282 |
| 5,968,547 A | 10/1999 | Reder et al. | 424/449 |
| 6,231,866 B1 | 5/2001 | Mann | 424/449 |
| 6,344,212 B1 | 2/2002 | Reder et al. | 424/449 |

FOREIGN PATENT DOCUMENTS

WO    9619975    12/1994

OTHER PUBLICATIONS

Imoto et al., Biol. Pharm. Bull., vol. 19 (2), pp. 263-267, 1996.*
Stinchcomb et al, Pharmaceutical Research, vol. 12(10), pp. 1526-1529, 1995.*

* cited by examiner

*Primary Examiner*—Zinna N. Davis
(74) *Attorney, Agent, or Firm*—Davidson, Davidson and Kappel, LLC

(57) ABSTRACT

Disclosed are prodrugs and analogs of buprenorphine.

16 Claims, No Drawings

ANALOGS AND PRODRUGS OF BUPRENORPHINE

This application claims priority from U.S. Provisional Application Ser. No. 60/421,347, filed on Oct. 25, 2002 the disclosure of which is hereby incorporated by reference in its entirety.

BACKGROUND OF THE INVENTION

Buprenorphine, a partially synthetic opiate, has been contemplated for prolonged analgesia via transdermal formulations. Buprenorphine transdermal delivery systems are of particular interest because buprenorphine is a potent, partial agonist opioid analgesic with desirable therapeutic properties. For example, buprenorphine is 50 to 100 times more potent than morphine, but has a much safer therapeutic index than morphine (see Wallenstein S L, et al., *Crossover Trials in Clinical Analgesic Assays: Studies of Buprenorphine and Morphine*, Pharmacotherapy, G(5): 225–235, 1986). Further, the partial agonist properties of buprenorphine are useful in the treatment of opioid addiction.

There are several types of transdermal formulations of buprenorphine reported in the literature. See, for example, U.S. Pat. No. 5,240,711 (Hille et al.), U.S. Pat. No. 5,225,199 (Hidaka et al.), U.S. Pat. No. 5,069,909 (Sharma et al.), U.S. Pat. No. 4,806,341 (Chien et al.), and U.S. Pat. No. 5,026,556 (Drust et al).

The transdermal delivery of buprenorphine presents challenges to the pharmaceutical formulator as up to 70% or more buprenorphine is left in the patch after use due to the fact that buprenorphine exhibits poor skin penetration. This presents problems with formulating the dosage form and ensuring that a non-variable dosage is delivered as prescribed. Also, the large amount of residual buprenorphine remaining in the patch after use can be subject to abuse and diversion.

There exists a need in the art for a transdermal application of a compound which has the benefits of buprenorphine while minimizing the associated formulation, dosing and abuse problems discussed above.

OBJECTS AND SUMMARY OF THE INVENTION

In certain embodiments, the present invention is directed to a prodrug of buprenorphine represented by Formula I below:

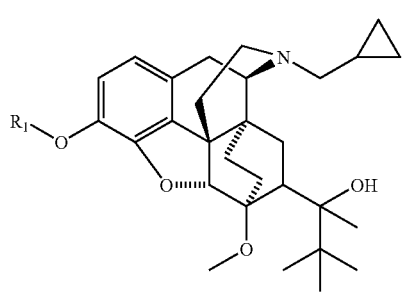
(I)

wherein $R_1$ is a moiety selected from the group consisting of alkylcarbonyl, alkenylcarbonyl arylcarbonyl, heteroarylcarbonyl, alkoxycarbonyl, aryloxycarbonyl and heteroaryloxycarbonyl moieties wherein the alkyl moiety is selected from the group consisting of unsubstituted or substituted, straight-chain, branched-chain and cyclic alkyl moieties having 1–20 carbon atoms; wherein the alkenyl moiety is selected from the group consisting of unsubstituted and substituted, straight-chain, branched-chain and cyclic alkenyl moieties having 2–20 carbon atoms; wherein the aryl moiety is selected from the group consisting of unsubstituted and substituted phenyl, and phenalkyl moieties wherein the alkyl moiety contains 1–3 carbon atoms and the phenyl moiety is unsubstituted or substituted; and the heteroaryl moiety is a substituted or unsubstituted aromatic 5-or 6-membered heterocyclic ring containing one or two heteroatoms selected from the group consisting of nitrogen, oxygen, and sulfur; and pharmaceutically acceptable salts thereof.

Examples of suitable straight-chain alkyl moieties in Formula I include methyl, ethyl, propyl, butyl, hexyl, heptyl, octyl, dodecyl and palnityl moieties and the like.

Examples of suitable branched-chain alkyl moieties include isopropyl, sec-butyl, t-butyl, 2-methylbutyl, 2-pentyl and 3-pentyl moieties and the like.

Examples of suitable cyclic alkyl moieties include cyclopropyl, cyclobutyl, cyclopentyl and cyclohexyl moieties and the like.

Examples of suitable "alkenyl" moieties include vinyl (ethenyl), 1-propenyl, i-butenyl, pentenyl, hexenyl, n-decenyl and c-pentenyl and the like.

The moieties may be substituted, generally with 1 or 2 substituents, wherein the substituents are independently selected from halo, hydroxy, alkoxy(alkoxy)x, hydroxyalkoxy(alkoxy)x, amino, mono- and dialkylamino, nitro, carboxyl, alkoxycarbonyl, and cyano moieties, wherein x is an integer from 0 to 3 and the alkoxy moieties contain from 1 to 5 carbon atoms.

By the expression "phenalkyl moieties wherein the alkyl moiety contains 1–3 carbon atoms" is meant benzyl, phenethyl and phenylpropyl moieties wherein the phenyl moiety may be substituted. When substituted, the phenyl moiety of the phenalkyl group may contain 1–3 substituents independently selected from alkyl, hydroxy, alkoxy, halo, amino, mono- and dialkylamino, nitro, carboxyl, alkoxycarbonyl and cyano moieties.

Examples of suitable "heteroaryl" moieties are pyridinyl, thienyl and imidazolyl.

The expression "halo" is meant in the conventional sense to include F, Cl, Br, and I.

Among the compounds represented by the general Formula I, particular examples of compounds are those in which $R_1$ is selected from group consisting of acetyl; propionyl; butyryl; valeryl; hexanoyl; isobutyryl; methoxyacetyl; ethoxyacetyl; benzoyl; nicotinoyl; methoxycarbonyl; ethoxycarbonyl; propoxycarbonyl; butoxycarbonyl; hexyloxycarbonyl; octyloxycarbonyl; and, imidazolylcarbonyl.

In certain embodiments, the present invention is directed to an analog of buprenorphine represented by Formula II below:

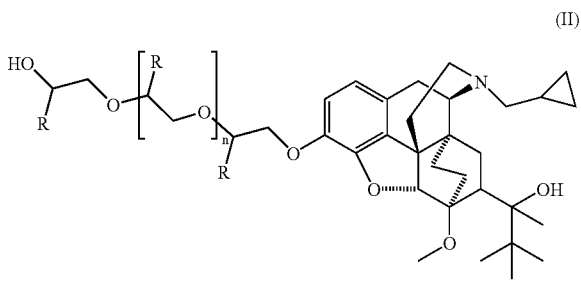

(II)

wherein n is an integer from 0 to 3 and each R is independently selected from the group consisting of hydrogen, methyl and ethyl.

In certain embodiments, the present invention is directed to a prodrug of buprenorphine, represented by Formula III below:

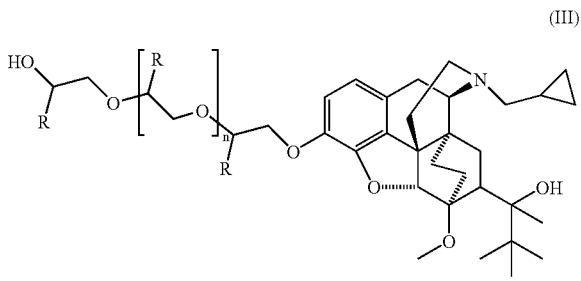

(III)

wherein n is an integer from 0 to 3 and each R is independently selected from the group consisting of hydrogen, methyl and ethyl.

In certain embodiments, the present invention is directed to pharmaceutical compositions comprising prodrugs of buprenorphine represented by Formula I or III and a pharmaceutically acceptable excipient.

In certain embodiments, the present invention is directed to analogs of buprenorphine represented by Formula II and a pharmaceutically acceptable excipient.

It is a further object of the present invention to prepare a pharmaceutical composition comprising combining a compound of Formula I, II or III with a pharmaceutically acceptable carrier.

It is a further object of the present invention to provide a method for the treatment of pain in patients comprising applying to the skin of the patient an effective amount of a compound of Formula I, II or III.

It is a further object of certain embodiments of the invention to provide compounds of Formula I, II or III, which exhibit increased skin penetration compared to buprenorphine.

It is a further object of certain embodiments of the invention to provide a transdermal patch comprising a compound of Formula I, II or III, which has a reduced percentage of active agent remaining in the used patch as compared to buprenorphine.

For purposes of the present invention, the term "buprenorphine" shall include buprenorphine base, pharmaceutically acceptable salts thereof, stereoisomers thereof, and mixtures thereof.

DETAILED DESCRIPTION

The buprenorphine prodrug of the present invention, i.e., compounds of Formula I and III, preferably demonstrate a higher lipophilicity and biphase solubility than the active parent drug and hence are better able to penetrate the skin of a human or non-human animal and are capable of reverting to the active buprenorphine during or after penetration through the skin. These characteristics make the prodrugs useful for transdermal delivery of buprenorphine.

The buprenorphine analogs of the of the present invention, i.e. compounds of Formula II, preferably demonstrate better absorption characteristics than buprenorphine in order to promote the active agent being absorbed by the skin. The analogs can be prepared by modifying buprenorphine with ethylene oxide, propylene oxide, butylene oxide or a mixture thereof.

The compositions according to the present invention can be combined with a drug delivery device such as a patch, gauze or compress. The compositions are also suitable for topical or intranasal application as an ointment, cream, lotion, paste, gel, spray, aerosol and oil. Suitable carriers for such formulations include petroleum jelly, lanolin, polyethylene glycols, alcohols, and combinations thereof.

In certain embodiments of the present invention, the compounds of the present invention are administered transdermally. Preferable transdermal delivery systems include transdermal patches, transdermal plasters, transdermal discs, iontophoretic transdermal devices and the like.

Transdermal dosage forms used in accordance with the invention can include a backing layer made of pharmaceutically acceptable material which is impermeable to a compound of the present invention. The backing layer preferably serves as a protective cover for compound, and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films and textile fabrics. Preferably, the materials used for the backing layer are laminates of such polymer films with a metal foil such as aluminum foil. The backing layer can be any appropriate thickness which will provide the desired protective and support functions. A suitable thickness will be from about 10 to about 200 microns. Desirable materials and thickness will be apparent to the skilled artisan.

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

Preferred materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable cross-linking agent. Suitable crosslinking agents include, e.g., tetrapropoxysilane.

Preferred transdermal delivery systems used in accordance with the methods of the present invention include an adhesive layer to affix the dosage form to the skin of the patient for a desired period of administration, e.g., about 1 to about 7 days. If the adhesive layer of the dosage form fails to provide adhesion for the desired period of time, it is possible to maintain contact between the dosage form and the skin by, for instance, affixing the dosage form to the skin of the patient with an adhesive tape, e.g, surgical tape. It is not critical for purposes of the present invention whether adhesion of the dosage form to the skin of the patient is achieved solely by the adhesive layer of the dosage form or in connection with a peripheral adhesive source, such as surgical tape, provided that the dosage form is adhered to the patient's skin for the requisite administration period.

The adhesive layer preferably includes using any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the compounds of the general Formula I, buprenorphine analogs and buprenorphine prodrugs into the blood stream of the patient. A non-limiting list of permeation enhancing agents includes polyethylene glycols, surfactants, and the like.

Alternatively, permeation of the compounds of the present invention may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal dosage form. Other means of enhancing permeation of the compounds of the present invention such as the use of iontophoretic means are also contemplated to be within the scope of the present invention.

In certain embodiments, the transdermal dosage form which may be used in accordance with the present invention includes a non-permeable backing layer made, for example, of polyester; an adhesive layer made, for example of a polyacrylate; and a matrix containing the compound of the present invention and other desirable pharmaceutical aids such as softeners, permeability enhancers, viscosity agents and the like.

The active agent may be included in the device in a drug reservoir, drug matrix or drug/adhesive layer.

Certain preferred transdermal delivery systems also include a softening agent. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids and coconut oil. Further examples of suitable softeners are multivalent alcohols, for example, levulinic acid, glycerol and 1,2-propanediol which can also be etherified by polyethylene glycols.

A solvent may also be included in the transdermal delivery systems of the present invention. A non-limiting list of suitable solvents include those with at least one acidic moiety. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the materials used for the production of the backing layer described above provided that they are rendered removable, for example, by a silicone treatment. Other removable protective layers, for example, are polytetra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

Certain preferred transdermal dosage forms for use in accordance with the present invention are described in U.S. Pat. No. 5,240,711 (Hille, et. al.; assigned to LTS Lohmann Therapie-Systeme GmbH & Co.). The transdermal delivery device described therein includes a backing layer which is impermeable to the buprenorphine, a pressure-sensitive adhesive reservoir layer and optionally, a removable protective layer. Preferably, the reservoir layer includes about 10 to about 95%-wt polymeric material, about 0.1 to about 40%-wt softener, about 0.1 to about 30%-wt buprenorphine. A solvent for the buprenorphine base or pharmaceutically acceptable salt thereof may be included as about 0.1 to about 30%-wt.

In a preferred embodiment, the transdermal delivery system is prepared in accordance with the disclosure of International Patent Application No. WO 96/19975 (Hille, et. al.; assigned to LTS Lohmann Therapie-Systeme GMBH). In this device, the transdermal delivery device contains resorption-promoting auxiliary substances. The resorption-promoting auxiliary substance forms an undercooled mass. The delivery system contains 10% buprenorphine base, 10–15% acid (such as levulinic acid), about 10% softener (such as oleyoleate), 55–70% polyacrylate, and 0–10% polyvinylpyrollidone (PVP).

In other embodiments, the transdermal delivery system may be a plaster such as that described in U.S. Pat. No. 5,225,199 to Hidaka et al. Such plasters include a film layer including a polyester film of about 0.5 to about 4.9 µm thickness, about 8 to about 85 g/mm strength, respectively in the two directions intersecting substantially at right angles, about 30 to about 150% elongation, in the two directions intersecting substantially at right angles and an elongation ratio of A to B of about 1.0 to about 5.0, wherein A and B represent data in two directions intersecting at right angles, and A is greater than B and wherein said polyester film includes about 0.01 to about 1.0% by weight, based on the total weight of the polyester film, of solid fine particles in which the average particle size is about 0.001 to about 3.0 µm and an adhesive layer which is composed of an adhesive containing transdermally absorbable drugs; wherein the adhesive layer is laminated on said film layer over the surface in about 2 to about 60 µm thickness. The average particle size is substantially not more than 1.5 times the thickness of the polyester film.

The transdermal delivery system used in the present invention may alternatively be prepared in accordance with U.S. Pat. No. 5,069,909 (Sharma et al.). This patent describes a laminated composite which includes an impermeable backing layer providing a protective covering for the composite which may be made from an elastomeric polymer such as polyurethane, polyether amide, or copolyester and may be about 15–250 microns in thickness. The composite further includes a reservoir lamina composed of the drug in an amount of 1–12% by weight and a pressure-sensitive adhesive, e.g., polyisobutylene, or a silicone adhesive such as silastic, or an acrylate adhesive, and 2–35% permeation enhancer (comprising propylene glycol monolaurate in combination with capric acid or oleic acid).

The transdermal delivery system used in the present invention may alternatively be prepared in accordance with U.S. Pat. No. 4,806,341 (Chien et al.). This patent describes a transdermal system of a pharmaceutical polymer matrix dosage unit having a backing layer which is substantially impervious to the drug, and a polymer matrix disc layer which is adhered to the backing layer and which has microdispersed therein effective dosage amounts of the drug. The polymer matrix may be a silicon polymer or copolymer, such as methyl silicone polymer or copolymer, or methylvinyl silicone polymer or copolymer. The polymer matrix layer preferably has dispersed therein a skin permeation enhancing agent such as isopropyl myristate, azone, or a combination of ethyl caprylate and capryl alcohol.

The transdermal delivery system used in the present invention may alternatively be prepared in accordance with U.S. Pat. No. 5,026,556 (Drust et al.). Described therein are compositions of the drug in a carrier of a polar solvent material selected from the group consisting of $C_3$–$C_4$ diols, $C_3$–$C_6$ triols, and mixtures thereof, and a polar lipid material selected from the group consisting of fatty alcohol esters, fatty acid esters, and mixtures thereof; wherein the polar solvent material and the lipid material are present in a weight ratio of solvent material:lipid material of from 60:40 to about 99:1.

The transdermal delivery system used in the present invention may alternatively be prepared in accordance with U.S. Pat. No. 4,588,580 (Gale, et. al.). This system comprises a reservoir for the drug having a skin proximal, material releasing surface area in the range of about 5–100 $cm^2$ and containing between 0.1 and 50% by weight of the drug. The reservoir contains an aqueous gel comprising up to about 47–95% ethanol, 1–10% gelling agent, 0.1–10% drug, and release rate controlling means disposed in the flow path of the drug to the skin which limits the flux of the drug from the system through the skin. The release rate controlling means is more permeable to the drug than to the ethanol, and may be, for example, low density polyethylene (LDPE), ethylene-vinyl acetate (EVA) copolymers, heat sealable polyesters, and elastomeric polyester block copolymers, such as HYTREL® from DuPont. This system is said to be capable of providing an administration rate of about 10–300 µg/hr.

It is contemplated that each of the transdermal delivery systems described herein may be modified by incorporating a compound of the present invention to effect transdermal delivery of the compound. Such modifications are within the abilities of one skilled in the art of formulating transdermal delivery systems.

The prodrugs or analogs of the present invention can also be included in a pharmaceutical composition selected from the group consisting of an oral, sublingual, implantable, intranasal, inhalable and parenteral dosage forms. When the prodrugs or analogs are present in oral dosage forms, the agent can be combined with excipients, i.e., pharmaceutically acceptable organic or inorganic carrier substances suitable for oral administration which are known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical compositions can be sterilized and if desired mixed with auxiliary agents, e.g., lubricants, preservatives, stabilizers, wetting agents, emulsifiers, salts for influencing osmotic pressure buffers, coloring, flavoring and/or aromatic substances.

The oral pharmaceutical compositions of the present invention can be in the form of tablets, dragees, liquids, drops, gelcaps, troches, lozenges, aqueous or oily suspensions, multiparticulate formulations including dispersable powders, granules, pellets, matrix spheroids or coated inert beads, emulsions, hard or soft capsules or syrups or elixirs, microparticles (e.g., microcapsules, microspheres and the like), buccal tablets, etc.

The compositions intended for oral use may be prepared according to any method known in the art and such compositions may contain one or more agents selected from the group consisting of inert, non-toxic pharmaceutically acceptable excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions preferably contain the prodrugs or analogs thereof in a mixture that has one or more excipients suitable as suspending agents, for example, pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used, wherein a sweetened vehicle is employed. Injectable suspensions may also be prepared, in which case appropriate liquid carriers, suspending agents and the like may be employed.

The pharmaceutical compositions comprising the prodrugs or analogs of the present invention can be prepared as immediate or sustained release formulations. For example, a sustained release carrier can be included in the formulation to provide a release of the agent or salt thereof over a 12 to 24 hour period.

In certain embodiments the oral dosage form includes a sustained-release material which is incorporated into a matrix along with the prodrugs or analogs to provide for the sustained release of the agent. The sustained-release material may be hydrophobic or hydrophilic as desired. The oral dosage form of the present invention may be prepared as granules, spheroids, matrix multiparticulates, etc. which comprise the prodrugs or analogs in a sustained release matrix, which may be compressed into a tablet or encapsulated. The oral dosage form of the present invention may optionally include other pharmaceutically acceptable ingredients (e.g., diluents, binders, colorants, lubricants, etc.).

In certain embodiments, the oral dosage form of the present invention may be an osmotic dosage form having a push or displacement composition as one of the layers of a bilayer core for pushing the prodrugs or analogs from the dosage form, and a semipermeable wall composition surrounding the core, wherein the wall has at least one exit means or passageway for delivering the naltrexone from the dosage form. Alternatively, the core of the osmotic dosage form may comprise a single layer core including a controlled release polymer and the prodrugs or analogs.

All of the references cited herein, including the foregoing, are hereby incorporated by reference in their entireties for all purposes.

The following examples illustrate various aspects of the present invention. They are not to be construed to limit the claims in any manner whatsoever.

EXAMPLE 1

Preparation of 3,6-dipropionyl buprenorphine

A mixture of buprenorphine and propionic anhydride is stirred at a suitable temperature. Upon cooling to room temperature, water is added. The solution is partitioned between ether and potassium hydroxide solution. The ether phase is separated, washed with water, dried over anhydrous sodium sulphate and evaporated in vacuo. The residue obtained is crystallized from ethanol-water to yield the title compound.

EXAMPLE 2

Preparation of 3-propionyl buprenorphine

Propionic anhydride is added while stirring to a mixture of sodium bicarbonate and buprenorphine hydrochloride in water. After complete addition the mixture is stirred and extracted with chloroform. The combined extracts are dried over anhydrous sodium sulphate and evaporated in vacuo to yield the title compound.

EXAMPLE 3

Preparation of 3,6-diisobutyryl buprenorphine

The compound is prepared as described in Example 1, using isobutyric anhydride instead of propionic anhydride. The compound is recrystallized from ether-petroleum ether.

EXAMPLE 4

3,6-dihexanoyl buprenorphine

The compound is prepared as described in Example 1, using hexanoic anhydride instead of propionic anhydride.

EXAMPLE 5

Preparation of 3-hexanoyl buprenorphine

The compound is prepared as described in Example 2, using the equivalent amount of hexanoic anhydride instead of propionic anhydride.

We claim:

1. A compound of Formula I:

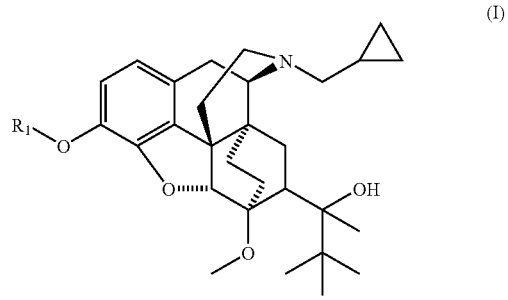

(I)

wherein $R_1$ is a moiety selected from the group consisting of alkylcarbonyl, alkenylcarbonyl, arylcarbonyl, heteroarylcarbonyl, alkoxycarbonyl, aryloxycarbonyl and heteroaryloxycarbonyl moieties;

wherein the alkyl portion of the alkylcarbonyl moiety is selected from the group consisting of unsubstituted and substituted, straight-chain and branched-chain alkyls having from 8 to 20 carbon atoms; or wherein the alkyl portion of the alkyl carbonyl moiety is a cyclic alkyl having from 3 to 20 carbon atoms;

wherein the alkenyl portion of the alkenylcarbonyl moiety is selected from the group consisting of unsubstituted and substituted, straight-chain and branched-chain and cyclic alkenyl moieties having from 2 to 20 carbon atoms;

wherein the aryl portion of the arylcarbonyl moiety is selected from the group consisting of unsubstituted and substituted phenyl, and phenylalkyl; wherein the alkyl portion of the phenylalkyl contains from 1 to 3 carbon atoms; wherein the phenyl portion of the phenylalkyl is unsubstituted or substituted;

wherein the heteroaryl portion of the heteroarylcarbonyl moiety is an aromatic 5- or 6-membered heterocyclic ring containing one or two heteroatoms selected from the group consisting of nitrogen, oxygen, and sulfur; or a pharmaceutically acceptable salt thereof.

2. The compound according to claim 1, wherein said straight-chain alkyl is selected from the group consisting of octyl, dodecyl, and palmityl; and said straight-chain alkyl is optionally substituted with 1 or 2 substituents independently selected from the group consisting of halo, hydroxy, alkoxy (alkoxy)x, hydroxyalkoxy(alkoxy)x, amino, monoalkylamino, dialkylamino, nitro, carboxyl, alkoxycarbonyl, and cyano, wherein x is an integer from 0 to 3 and the alkoxy contains from 1 to 5 carbon atoms.

3. The compound according to claim 1, wherein said cyclic alkyl is selected from the group consisting of cyclopropyl, cyclobutyl, cyclopentyl and cyclohexyl; and said cyclic alkyl is optionally substituted with 1 or 2 substituents independently selected from the group consisting of halo, hydroxy, alkoxy(alkoxy)x, hydroxyalkoxy(alkoxy)x, amino, monoalkylamino, dialkylamino, nitro, carboxyl, alkoxycarbonyl, and cyano, wherein x is an integer from 0 to 3 and the alkoxy portion of the alkoxycarbonyl contains from 1 to 5 carbon atoms.

4. The compound according to claim 1, wherein said alkenyl is selected from the group consisting of vinyl, 1-propenyl, i-butenyl, pentenyl, hexenyl, n-decenyl and c-pentenyl; and said alkenyl is optionally substituted with 1 or 2 substituents independently selected from the group consisting of halo, hydroxy, alkoxy(alkoxy)x, hydroxyalkoxy(alkoxy)x, amino, monoalkylamino, dialkylamino, nitro, carboxyl, alkoxycarbonyl, and cyano, wherein x is an integer from 0 to 3 and the alkoxy portion of the alkoxycarbonyl contains from 1 to 5 carbon atoms.

5. The compound according to claim 1, wherein said phenylalkyl is selected from the group consisting of benzyl, phenylethyl and phenylpropyl; and the phenyl portion of the phenylalkyl is optionally substituted with 1 to 3 substituents independently selected from the group consisting of alkyl, hydroxy, alkoxy, halo, amino, monoalkylamino, dialkylamino, nitro, carboxyl, alkoxycarbonyl and cyano.

6. The compound according to claim 1, wherein said heteroaryl is selected from the group consisting of pyridinyl, thienyl and imidazolyl.

7. The compound according to claim 1, wherein $R_1$ is selected from group consisting of methoxyacetyl; ethoxyacetyl; benzoyl; nicotinoyl; methoxycarbonyl; ethoxycarbonyl; propoxycarbonyl; butoxycarbonyl; hexyloxycarbonyl; octyloxycarbonyl; and imidazolylcarbonyl.

8. A compound of Formula II:

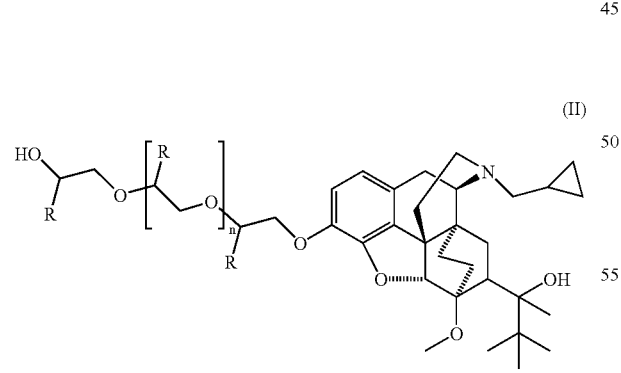

(II)

wherein n is an integer from 0 to 3 and each R is independently selected from the group consisting of hydrogen, methyl and ethyl; or a pharmaceutically acceptable salt thereof.

9. A compound of Formula III:

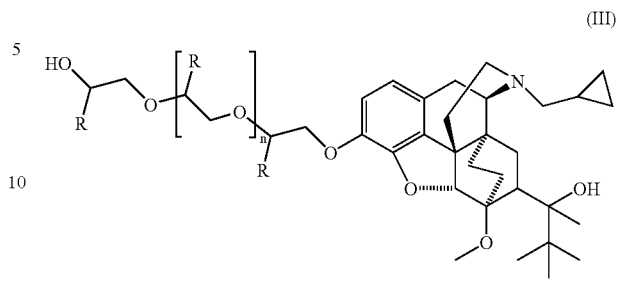

(III)

wherein n is an integer from 0 to 3 and each R is independently selected from the group consisting of hydrogen, methyl and ethyl; or a pharmaceutically acceptable salt thereof.

10. A pharmaceutical composition comprising a compound according to any of claims 1–9 and a pharmaceutically acceptable carrier.

11. The pharmaceutical composition according to claim 10, wherein said composition is in a form suitable for topical application selected from the group consisting of a transdermal patch, gauze, compress, ointment, cream, lotion, paste, gel, spray, aerosol and oil.

12. The pharmaceutical composition according to claim 11, wherein said form suitable for topical application is a transdermal patch.

13. The pharmaceutical composition of claim 10 in a form selected from the group consisting of an oral, sublingual, implantable, intranasal, inhalable and parenteral dosage form.

14. A method for preparing a pharmaceutical composition comprising combining a pharmaceutically acceptable excipient with a compound of any of claims 1–9.

15. A method for the treatment of pain in a patient in need thereof comprising applying to the skin of the patient an effective amount of a compound of any of claims 1–9.

16. A pharmaceutical composition comprising a compound of Formula I:

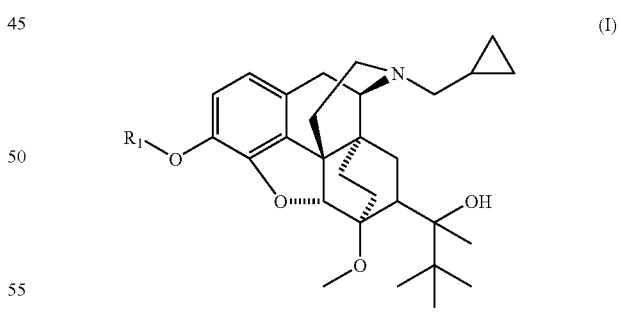

(I)

wherein $R_1$ is a moiety selected from the group consisting of alkylcarbonyl, alkenylcarbonyl, arylcarbonyl, heteroarylcarbonyl, alkoxycarbonyl, aryloxycarbonyl and heteroaryloxycarbonyl moieties;

wherein the alkyl portion of the alkylcarbonyl moiety is selected from the group consisting of unsubstituted and substituted, straight-chain and branched-chain alkyls having from 8–20 carbon atoms; or wherein the alkyl portion of the alkyl carbonyl moiety is a cyclic alkyl having from 3 to 20 carbon atoms;

wherein the alkenyl portion of the alkenylcarbonyl moiety is selected from the group consisting of unsubstituted and substituted, straight-chain and branched-chain and cyclic alkenyl moieties having from 2 to 20 carbon atoms;

wherein the aryl portion of the arylcarbonyl moiety is selected from the group consisting of unsubstituted and substituted phenyl, and phenylalkyl; wherein the alkyl portion of the phenylalkyl contains from 1 to 3 carbon atoms; wherein the phenyl portion of the phenylalkyl is unsubstituted or substituted;

wherein the heteroaryl portion of the heteroarylcarbonyl moiety is an aromatic 5- or 6-membered heterocyclic ring containing one or two heteroatoms selected from the group consisting of nitrogen, oxygen, and sulfur;

or a pharmaceutically acceptable salt thereof; and a pharmaceutically acceptable carrier;

wherein the composition is in a form selected from the group consisting of an oral, sublingual, implantable, intranasal, inhalable and parenteral dosage form.

* * * * *